United States Patent [19]

Chao et al.

[11] 4,252,111

[45] Feb. 24, 1981

[54] LOCKING MECHANISM FOR ORTHOPEDIC BRACES

[76] Inventors: James C. Fletcher, Administrator of the National Aeronautics and Space Administration, with respect to an invention of Jireh I. Chao, Philadelphia, Pa.; Charles H. Epps, Jr., Washington, D.C.

[21] Appl. No.: 798,976

[22] Filed: May 20, 1977

Related U.S. Application Data

[63] Continuation of Ser. No. 676,958, Apr. 14, 1976, abandoned.

[51] Int. Cl.$^3$ .................................. A61F 5/01
[52] U.S. Cl. ............................................. 128/80 F
[58] Field of Search ............... 128/80 F, 80 C, 80 R, 128/80 H, 77, 88; 3/27; 403/113, 117

[56] References Cited

U.S. PATENT DOCUMENTS

| | | | |
|---|---|---|---|
| 1,477,070 | 12/1923 | Martin | 128/88 |
| 1,750,213 | 3/1930 | Collins | 128/80 F X |
| 2,558,986 | 7/1951 | Seelert | 128/80 F |
| 2,573,866 | 11/1951 | Murphy | 128/80 F |

*Primary Examiner*—Robert W. Michell
*Assistant Examiner*—Michael H. Thaler
*Attorney, Agent, or Firm*—Robert D. Marchant; John R. Manning; John O. Tresansky

[57] ABSTRACT

A locking mechanism for orthopedic braces includes upper and lower brace members pivotably jointed together, notched or recessed plates being fixedly secured to the lower brace member while a U-shaped locking bar is pivotably secured to the upper brace member for lockingly cooperating with the notched or recessed plates, a spring-biased actuating lever being operatively associated with the U-shaped locking bar. The upper and lower brace members are also provided with drilled holes or bores which are angularly oriented with respect to the longitudinal axes of the upper and lower brace members, the bores being aligned with each other when the longitudinal axes of the brace members are likewise aligned.

A freely movable pin is slidably disposed within the bores, the outer ends of the bores being suitably capped so as to retain the pin therewithin, and when the brace is vertically disposed so as to simulate standing or walking conditions, both brace members also being longitudinally aligned, the U-shaped locking bar automatically lockingly engages the recessed or notched plates while the slidable pin is interposed between both brace members and within both bores thereof, thereby preventing the occurrence of relative pivoting between the brace members. When the brace is alternatively disposed in a suitably inclined position, corresponding to simulated sitting conditions, the pin moves solely into the bore of the upper brace member thereby permitting relative pivoting to occur between the brace members when the U-shaped locking bar is disengaged from the notched plates by means of the actuating lever.

9 Claims, 9 Drawing Figures

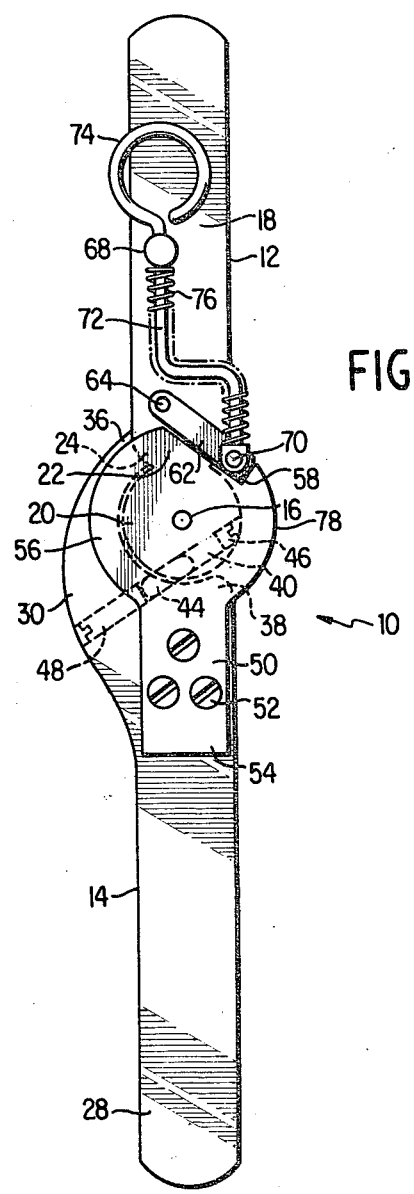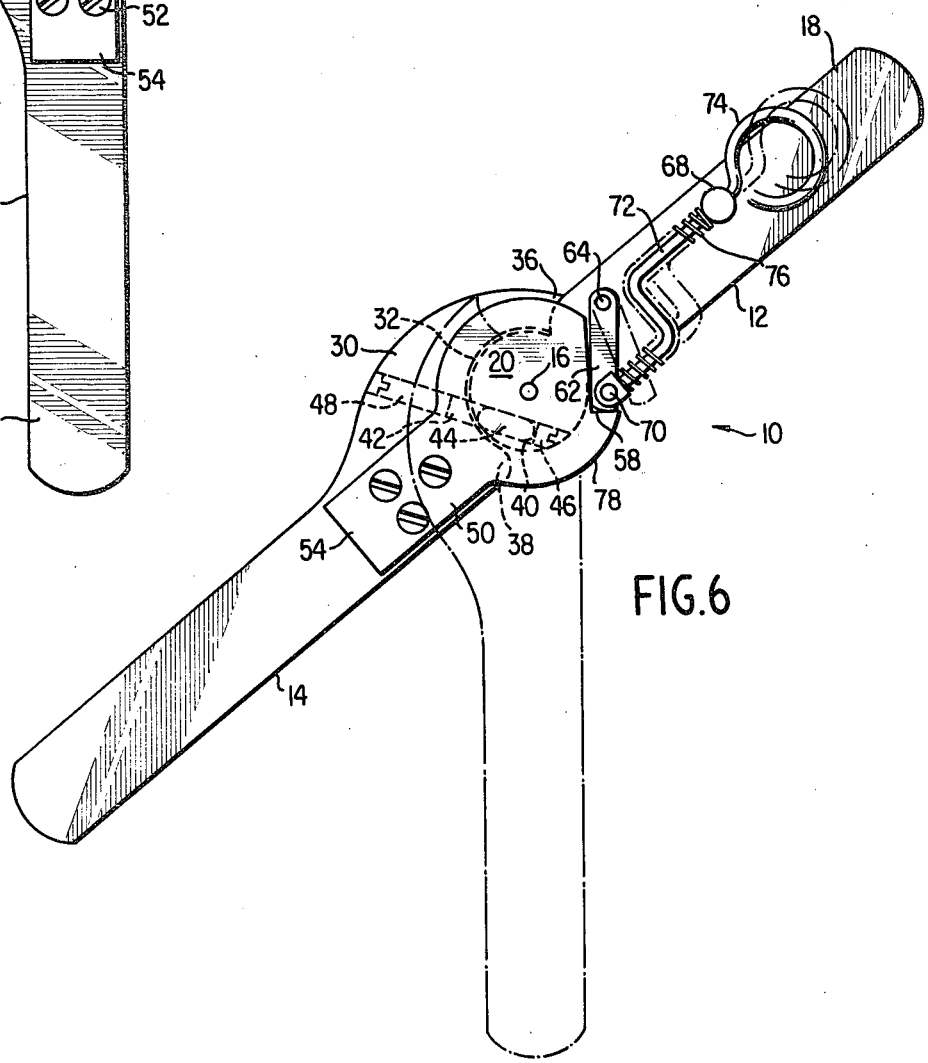

LOCKING MECHANISM FOR ORTHOPEDIC BRACES

ORIGIN OF THE INVENTION

The invention described herein was made in the performance of work under a NASA contract and is subject to the provisions of section 305 of the National Aeronautics and Space Act of 1958, Public Law 85-568(72 Stat. 435; 42 U.S.C. 245 7).

This is a continuation, of application serial no. 676,958, filed Apr. 14, 1976 now abandoned.

BACKGROUND OF THE INVENTION

1. Field of the Invention

The present invention relates generally to orthopedic braces, and more particularly to an improved locking mechanism for such braces.

2. Description of the Prior Art

While an innumerable variety of braces pervade the orthopedic field to assist the ambulation of handicapped and other afflicted persons, and while such braces may also include manually or automatically operable locking mechanisms for a variety of purposes, conventional locking mechanisms are capable of being unlocked under undesirable conditions and at undesirable times whereby the locking function of the brace may readily be circumvented and the constructive and rehabilitative purposes of the brace may likewise be thwarted.

The application of orthopedic braces, for example, to the lower extremities of children affected with spasticity and other neurological problems has been an effective means of preventing deformity and contracture while at the same time permitting ambulation under optimum extremity disposition. Unfortunately, however, as conventional orthopedic brace locking mechanisms characteristically exhibit the aforenoted disadvantage of being capable of being unlocked at inexpedient times, children are able to gain control over the opening and locking functions of the locking mechanisms of the braces and, despite admonitions from their parents, teachers, doctors, and the like, often unlock the same, whereupon walking, while such unlocked conditions prevail, causes for example, knee flexion and calcaneal deformities to recur.

SUMMARY OF THE INVENTION

Accordingly, it is an object of the present invention to provide a new and improved locking mechanism for orthopedic braces.

Another object of the present invention is to provide a new and improved orthopedic brace locking mechanism which, under standing or walking conditions, cannot be unlocked so as to effectively prevent bending of the knee portion of the brace, and consequently the knee portions of the person's braced lower extremities, yet nevertheless permitting the locking mechanism, under sitting conditions, to be simply unlocked, even by a child, so as to in fact permit bending of the patient's knees.

Still another object of the present invention is to provide a new and improved orthopedic brace locking mechanism which is rendered operable, and inoperable, in dependence upon the relative inclination of the brace with respect to the ground.

Yet another object of the present invention is to provide a new and improved orthopedic brace locking mechanism which is automatically locked under simulated standing or walking conditions and which may be simply manually unlocked under simulated sitting conditions.

A further object of the present invention is to provide a new and improved orthopedic brace locking mechanism which is light in weight and relatively small in size.

The foregoing and other objectives are achieved in accordance with the present invention through the provision of an orthopedic brace locking mechanism which includes upper and lower brace members pivotably joined together, notched, or recessed plates being fixedly secured to the lower brace member while a U-shaped locking bar is pivotably secured to the upper brace member for lockingly cooperating with the notched or recessed plates, a spring-biased actuating lever being operatively associated with the U-shaped locking bar. The upper and lower brace members are also provided with drilled holes or bores which are angularly oriented with respect to the longitudinal axes of the upper and lower brace members, the bores being aligned with each other when the longitudinal axes of the brace members are likewise aligned.

A freely movable pin is slidably disposed within the bores, the outer ends of the bores being suitably capped so as to retain the pin therewithin, and when the brace is vertically disposed, so as to simulate standing or walking conditions, both brace members also being longitudinally aligned, the U-shaped locking bar automatically lockingly engages the recessed or notched plates while the slidable pin is interposed between both brace members and within both bores thereof, thereby preventing the occurrence of relative pivoting between the brace members. When the brace is alternatively disposed in a suitably inclined position, corresponding to simulated sitting conditions, the pin moves solely into the bore of the upper brace member thereby permitting relative pivoting to occur between the brace members when the U-shaped locking bar is disengaged from the notched plates by means of the actuating lever.

BRIEF DESCRIPTION OF THE DRAWINGS

Various other objects, features, and attendant advantages of the present invention will be more fully appreciated as the same becomes better understood from the following detailed description when considered in connection with the accompanying drawings, in which like reference characters designate like or corresponding parts throughout the several views, and wherein:

FIG. 5 is a side elevation view of the brace of FIG. 4 disclosing the operation of the locking mechanism of the present invention under locked conditions; and FIG. 6 is a side elevation view of the brace of FIG. 4 disclosing the operation of the locking mechanism of the present invention under partially locked conditions.

DETAILED DESCRIPTION OF A PREFERRED EMBODIMENT

Figure 1A:
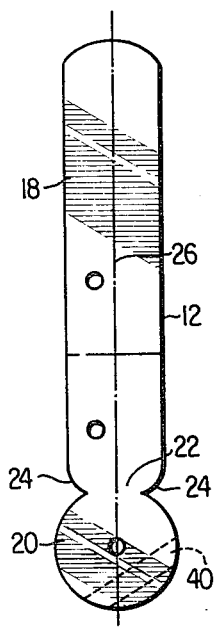
FIGS. 1a and 1b are side and front elevation views, respectively, of the upper brace member utilized within an orthopedic brace embodying the present invention.
Figure 1B:
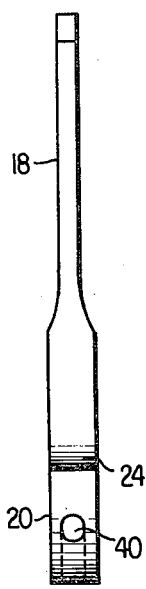
Figure 2A:
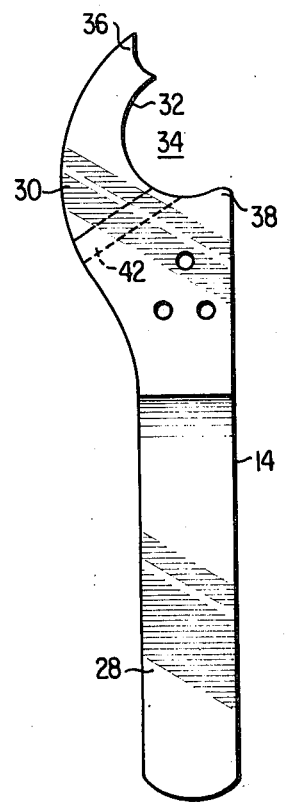
FIGS. 2a and 2b are views similar to those of FIGS. 1a and 1b, respectively, showing however, the lower brace member utilized within the brace embodying the present invention.
Figure 2B:
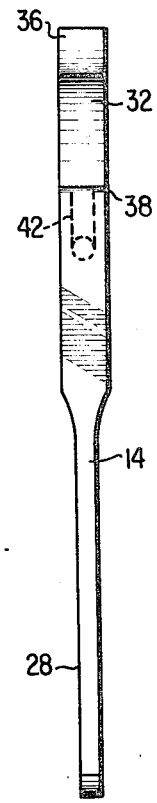
Figure 4:
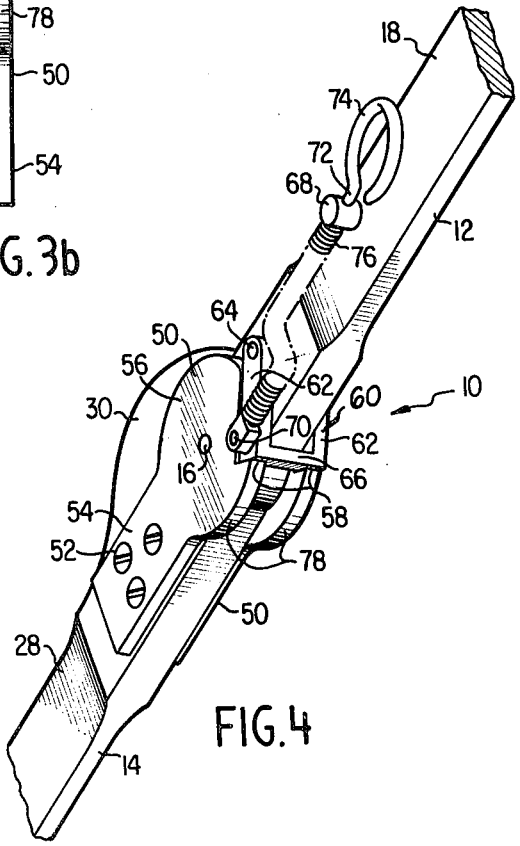
FIG. 4 is a perspective view of the assembled brace incorporating the locking mechanism of the present invention.

Referring now to the drawings, the orthopedic brace, within which the locking mechanism of the present invention is incorporated, is generally indicated by the reference character 10, as seen within FIGS. 4, 5 and 6, and is seen to include an elongate, upper plate member 12, as best seen in FIGS. 1a and 1b, and an elongate, lower plate member 14, as best seen in FIGS. 2a and 2b, pivotably secured together by means of a pivot pin 16, as seen in FIGS. 4, 5 and 6. As best seen within FIGS. 1a and 1b, the upper portion 18 of upper plate member 12 is substantially rectangular in configuration, while the lower portion 20 of plate member 12 is substantially circular in configuration, upper and lower portions 18 and 20, respectively, being integrally formed and secured together by means of a neck portion 22 which defines two arcuately configured shoulder portions 24 laterally disposed upon opposite sides of the longitudinal axis 26 of member 12.

As best seen within FIGS. 2a and 2b, the lower portion 28 of lower plate member 14 is likewise substantially rectangular in configuration, while the upper portion 30 of plate member 14 is substantially semi-circular in configuration. The interior surface 32 of portion 30 defines a semi-circular recess 34 having a radial or diametrical extent which is the same as, or slightly larger than, that of circular plate portion 20 of plate member 12 so as to pivotably mate therewith and thereby facilitate pivotable movement to occur between the plate members 12 and 14, and to limit the pivotable movement between plate members 12 and 14 corresponding to the aligned and bent dispositions of such members under simulated standing or sitting conditions, portion 30 of plate member 14 is additionally provided with diametrically opposed projections 36 and 38 which are adapted to mate with the shoulders 24 of plate member 12, it being particularly noted, as best seen, for example within FIG. 5, that the configuration of projection 36 coincides precisely with that of neck portion 22 and shoulder portion 24 of plate member 12 to positively arrest the pivotable movement of the plate members relative to one another when longitudinally aligned and to facilitate the locking of the same under simulated standing conditions.

Circular plate portion 20 of plate member 12 is further provided with a bore 40 disposed along a chord which is radially offset with respect to the center of portion 20, and semi-circular plate portion 30 of plate member 14 is likewise provided with a similarly disposed bore 42. Both bores are disposed at an approximate angle of 55° with respect to the longitudinal axes of members 12 and 14 and are adapted to be aligned with each other, as best seen, for example, within FIG. 5, when members 12 and 14 are longitudinally aligned. As illustrated within FIG. 5, an elongate pin 44, having rounded end portions, is freely slidable within bores 40 and 42, and to retain pin 44 therewithin, threaded members 46 and 48, such as, for example, Allen screws, are threadedly secured within the outer portions of the bores 40 and 42, respectively. The length of member 48, for example, is such that, when bores 40 and 42 are aligned as a result of plate members 12 and 14 being aligned and in the vertical position simulating standing conditions, the movement of pin 44, which moves downwardly within the bores under the influence of gravity, will be arrested at such a location that pin 44 will be interposed between portions 20 and 30 of plate members 12 and 14, respectively, and in this manner, pivoting of the plate members 12 and 14 with respect to each other is positively prevented. To the contrary, the length of member 46 is such that, when the plate members 12 and 14 are longitudinally aligned and are also inclined with respect to a horizontal plane, or the ground, as shown, for example, within FIG. 6, simulating sitting conditions, the pin 44 again moves relatively downwardly under the influence of gravity and its movement is arrested such that the pin 44 is disposed solely within bore 40 of plate portion 20, the relative disposition of pin 44 with respect to plate members 12 and 14 thereby facilitating the relative pivotable movement between members 12 and 14.

Figure 3A:
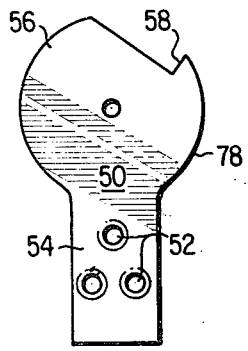
FIGS. 3a and 3b are views similar to those of FIGS. 1a and 1b, respectively, showing however the notched plates utilized within the brace embodying the present invention.
Figure 3B:
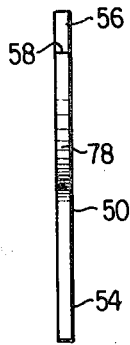

As can best be seen within FIGS. 3a, 3b, and 4, the lower plate member 14 is also provided with a pair of plates 50 which are fixedly secured upon the opposite side surfaces thereof by suitable fastening means 52. The lower portion 54 of each plate 50 is substantially rectangular in configuration so as to correspond to portion 28 of member 14, while the upper portion 56 of each plate 50 is substantially circular so as to correspond to semi-circular portion 30 of member 14, V-shaped notches 58 being respectively defined within upper portions 56 of plates 50. A substantially U-shaped locking bar 60, as seen in FIG. 4, the legs 62 of which, as seen within FIGS. 4–6, are disposed upon opposite sides of plate member 12, is pivotably secured to member 12, by means of a pivot pin 64, at a position substantially adjacent lower portion 20 of member 12 such that the crossbar 66 of bar 60 is permitted to be seated within the notched portions 58 of plates 50.

Referring to FIGS. 4, 5 and 6, a cylindrical projection 68 is fixedly secured, and extends perpendicularly to one side surface of the upper portion 18 of plate member 12, and a stud 70 is similarly disposed upon a side surface of locking bar 60 so as to be parallel with projection 68. Projection 68 is provided with a bore, not shown, and an actuating lever 72, having one end thereof secured, by suitable means, to stud 70, is slidably moveable through the bore of projection 68, the opposite end of lever 72 being formed with a fingergrip ring portion 74. A coil spring 76 is disposed about the portion of lever 72 interposed between projection 68 and stud 70, and in this manner, stud 70 and locking bar 60 will be spring-biased in a clockwise manner about pivot pin 64.

The operation of the locking mechanism of the orthopedic brace is thus quite apparent from the foregoing description. When the patient to which the brace is secured is in a simulated standing condition, as seen, for example, within FIG. 5, the plate members 12 and 14 will be longitudinally aligned and consequently, bores 40 and 42 will be similarly aligned whereby pin 44 will be interposed between members 12 and 14 thereby preventing pivotable movement therebetween. The actuating lever 72 is also disclosed within FIG. 5 as being spring-biased downwardly and consequently, locking bar 60, as seen in FIG. 4, is lockingly engaged with the notched portions 58 of plates 50.

If under these conditions, that is, simulated standing conditions, the patient were to desire to unlock the brace members so as to circumvent the locking function of the mechanism and to thwart the therapeutic purposes of the brace, the patient would grasp the fingergrip portion 74 of lever 72 and pull vertically upwardly so as to rotate locking bar 60 in the counterclockwise direction, against the biasing force of spring 76, and thereby disengage the same from notched portions 58, whereby the upper member 12 could then be attempted to be pivoted relative to lower member 14. However, due to the gravitational disposition of pin 44, relative pivotable movement between members 12 and 14 is nevertheless prevented.

To the contrary, if the patient were desirous of unlocking members 12 and 14 so as to attain relative pivotable movement therebetween in an effort to bend the knee portion of the brace and the afflicted extremity, the patient, under simulated sitting conditions as seen, for example, within FIG. 6, could grasp the fingergrip portion 74 of lever 72 and upon pulling in the direction away from lower plate member 14, rotate locking bar 60, as seen in FIG. 4, in the counterclockwise direction, against the biasing force of spring 76, and upon bar 60 clearing the notched portions 58 of plates 50, the lower plate member 14 will in fact pivot downwardly, as the gravitational disposition of pin 44 has already been altered such that the pin now resides solely within bore 40 of upper plate portion 20, the pivotable movement of plate member 14 being limited by means of projection 38 of lower plate portion 30. Under these pivotable conditions, the locking bar 60 is now disposed in contact with the small arcuate portion 78 of plate portion 56 of plates 50, and upon realigning plate members 12 and 14, locking bar 60, under the biasing force of spring 76, is snapped into engagement with notched portions 58 of plate 50 whereby the locking mechanism is again partially locked as disclosed within FIG. 6. Upon the patient rising from the sitting position to the standing position, pin 44 will again alter its disposition with respect to bores 40 and 42 and upon standing conditions being obtained, the locking mechanism is fully locked as disclosed within FIG. 5.

While the locking mechanism of the present invention has been particularly disclosed as including pin bores inclined with respect to the longitudinal axes of the plates members through an angle of approximately 55°, the mechanism will likewise operate efficiently if the angle is anywhere within the range of 50°-60°, although the range may depend somewhat upon the size of the patient's leg. It is to be noted that the pin is completely enclosed within the bores so as to protect the same from the environment whereby failsafe operation of the same is facilitated.

With respect to the materials employed within the various components of the mechanism, the gravity-actuated pin is preferably made of tungsten because of its high yield strength and stress resistance, and high mass, the pin only being subjected to stress if a patient tries to pivot the plate members while nevertheless standing. The pivot pin between the plate members is preferably made of steel, and based upon stress analysis, the brace can withstand the stresses imposed thereon by means of a 250 pound individual. The remaining components of the brace are made of aluminum which is substantially light in weight and malleable, the latter feature facilitating custom-fitting of braces to various patients, the braces being manufactured of prefabricated stock parts. While the tungsten pin might cause the pin bores of the aluminum brace members to wear and become oversized, a steel sleeve might be incorporated within the bores so as to line the same whereby the wear problem would be obviated.

Obviously, many modifications and variations of the present invention are possible in light of the above teachings. For example, in lieu of the gravity-pin mechanism, a spring-loaded, weight-bearing mechanism might be employed whereby, under standing conditions, the weight of the individual would compress the spring causing the latching mechanism to engage. Actuation of the locking bar type latching mechanism would nevertheless fail to disengage the spring-loaded mechanism and consequently, the brace would remain locked. Upon sitting, as the weight or load has been removed from the spring mechanism, unlatching of the same is permitted for bending the knee portion of the brace and extremity. It is to be understood therefore that within the scope of the appended claims, the present invention may be practiced otherwise than as specifically described herein.

What is claimed as new and desired to be secured by Letters Patent of the United States is:

1. A locking mechanism for an orthopedic brace, comprising:

an elongate upper brace member having a longitudinal axis and one end substantially cylindrical with an axis substantially perpendicular to said longitudinal axis and having a convex outer periphery;

an elongate lower brace member having a longitudinal axis and one end substantially formed as a crescent, said crescent's concave inner periphery having substantially the same radius as the convex outer periphery of said one end of said upper brace member, said crescent and cylindrical portions of said one ends of said upper and lower brace members being longitudinally and laterally opposed and radially aligned so that said crescent's concave inner periphery slidably engates said convex outer periphery of said one end of said upper brace member;

means for pivotably coupling said crescent and cylindrical portions of said one ends of said upper and lower brace members;

means defining a first bore, within said one end of said upper brace member, having a longitudinal axis lying in the same plane as said longitudinal axis of said upper brace member and inclined with respect to the longitudinal axis of said upper brace member by means of a predetermined angle;

means defining a second bore, within said crescent portion of said one end of said lower brace member, having a longitudinal axis lying in the same plane as said longitudinal axis of said lower brace member and inclined with respect to the longitudinal axis of said lower brace member by means of a predetermined angle which is the same as said angle of said first bore, and capable of being longitudinally aligned with said first bore when said upper and lower brace members are disposed with respect to each other in a predetermined manner; and pin means longitudinally slidable within said bores and being capable of longitudinally sliding within both of said bores and interposed between said crescent and cylindrical portions when said upper and lower brace members are disposed within a first position relative to a vertical plane to thereby prevent relative pivotable movement between said upper and lower brace members, and interposed solely within said bore of said cylindrical portion of said upper brace member when said upper and lower brace members are disposed within a second position relative to said vertical plane to permit relative pivotable movement between said upper and lower brace members.

2. A locking mechanism as set forth in claim 1, wherein:
said angle of inclination of said bores with respect to said longitudinal axes of said upper and lower brace members is within the range of 50°–60°.

3. A locking mechanism as set forth in claim 1, wherein:
said slidable pin means is a gravity-actuated pin.

4. A locking mechanism as set forth in claim 1, wherein:
said first and second bores extend through said upper and lower brace members, respectively; and
closure means are disposed within the outer ends of said bores for retaining said slidable pin means within said bores and for determining the extent of said longitudinally slidable movement, and the disposition, of said slidable pin means within said bores when said upper and lower members are disposed within said first and second positions.

5. A locking mechanism as set forth in claim 1, further comprising: additional means for preventing or permitting relative pivotable movement between said convex outer periphery of said cylinderical portion of said one end of said upper brace member and said cresent's concave inner periphery of of said one end of said lower brace member.

6. A locking mechanism as set forth in claim 5, wherein said additional means comprises:

plate means fixedly secured to said lower brace member, notched portions being defined within said plate means; and
locking means pivotably secured to said upper brace member engageable and disengageable with said notched portions of said plate means.

7. A locking mechanism as set forth in claim 6, further comprising:
manually operable lever means fixedly secured to said pivotable locking means and slidably disposed upon said upper brace member for disengaging said locking means from said notched portions of said plate means; and
spring means operatively associated with said lever means and said locking means for biasing said lever means and said locking means into engagement with said notched portions of said plate means,
whereby said locking means may be manually disengaged from said notched portions so as to permit relative pivotable movement between said cylindrical portion of said upper brace member and said crescent's concave inner periphery of said lower brace member and is automatically engageable with said notched portion under the influence of the biasing force of said spring means.

8. A locking mechanism as set forth in claim 7, further comprising:
ring-shaped fingergrip means integrally formed upon said lever means for facilitating said manual operation thereof.

9. A locking mechanism as set forth in claim 6, wherein:
said locking means is a U-shaped locking bar.

* * * * *